United States Patent [19]

Rivier et al.

[11] Patent Number: 5,112,809
[45] Date of Patent: May 12, 1992

[54] CRF ANALOGS

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 615,838

[22] Filed: Nov. 20, 1990

Related U.S. Application Data

[63] Continuation-in-part of Ser. No. 209,537, Jun. 21, 1988, abandoned.

[51] Int. Cl.⁵ ............... C07K 7/38; C07K 7/08; A61K 37/02
[52] U.S. Cl. .................... 514/12; 530/324; 930/DIG. 570
[58] Field of Search .............. 514/12; 530/324; 930/DIG. 570

[56] References Cited

U.S. PATENT DOCUMENTS 4,594,329  6/1986  Vale, Jr. et al. ............... 514/12
4,605,642  8/1986  River et al. .................... 514/12

OTHER PUBLICATIONS

Dayoff, M., Atlas of Protein Sequence and Structure, vol. 5: 89–99, 1972.

Vale, W. et al., "Conticotreopin-Releasing Factor", Encyclopedia of Neuroscience, G. Adelman (ed.), 1985.

Primary Examiner—Howard E. Schain
Assistant Examiner—Susan M. Perkins
Attorney, Agent, or Firm—Fitch, Even, Tabin & Flannery

[57] ABSTRACT

Analogs of CRF are disclosed that can be administered to achieve a substantial elevation of ACTH, β-endorphin, β-lipotropin, other products of the pro-opiomelanocortin gene and corticosterone levels and/or a lowering of blood pressure over an extended period of time. One analog which has been found to be particularly preferred is: [His$^{20}$, Nle$^{21}$, Leu$^{38}$]-rCRF. In the analogs, one or more of the first five N-terminals residues may be deleted or may be substituted by a peptide up to 10 amino acids long and/or by an acylating agent containing up to 7 carbon atoms. A number of other substitutions may also be made throughout the chain. These analogs or pharmaceutically or veterinarily acceptable salts thereof, dispersed in a pharmaceutically or veterinarily acceptable liquid or solid carrier, can be administered to mammels, including humans. These analogs may also be used as stimulants to elevate mood and improve memory and learning.

16 Claims, No Drawings

SEQUENCE LISTING (1) GENERAL INFORMATION:

(i) APPLICANT: Rivier, Jean E. F.
                  Vale Jr., Wylie W.

(ii) TITLE OF INVENTION: CRF ANALOGS (iii) NUMBER OF SEQUENCES: 40

(iv) CORRESPONDENCE ADDRESS:
      (A) ADDRESSEE: Fitch, Even, Tabin & Flannery
      (B) STREET: 135 South LaSalle Street, Suite 900
      (C) CITY: Chicago
      (D) STATE: Illinois
      (E) COUNTRY: USA
      (F) ZIP: 60603

(v) COMPUTER READABLE FORM:
      (A) MEDIUM TYPE: Floppy disk
      (B) COMPUTER: IBM PC compatible
      (C) OPERATING SYSTEM: PC-DOS/MS-DOS
      (D) SOFTWARE: PatentIn Release #1.24

(vi) CURRENT APPLICATION DATA:
      (A) APPLICATION NUMBER:
      (B) FILING DATE:
      (C) CLASSIFICATION:

(viii) ATTORNEY/AGENT INFORMATION:
      (A) NAME: Schumann, James J.
      (B) REGISTRATION NUMBER: 20856
      (C) REFERENCE/DOCKET NUMBER: 50739

(ix) TELECOMMUNICATION INFORMATION:
      (A) TELEPHONE: (619)552-1311
      (B) TELEFAX: (619)552-0095

(2) INFORMATION FOR SEQ ID NO:1:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:1:

Xaa Xaa Xaa Xaa Pro Ile Ser Xaa Xaa Leu Xaa Xaa Xaa Xaa Leu Arg
1               5                   10                  15

Xaa Xaa Xaa Xaa Xaa Xaa Xaa Xaa Xaa Xaa Xaa Xaa Xaa Gln Ala Xaa
                20                  25                  30

Xaa Asn Arg Xaa Xaa Xaa Xaa Xaa Xaa
            35                  40

(2) INFORMATION FOR SEQ ID NO:2:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:2:

Ser Gln Glu Pro Pro Ile Ser Leu Asp Leu Thr Phe His Leu Leu Arg
1               5                   10                  15

Glu Met Leu His Met Ala Lys Ala Glu Gln Glu Ala Glu Gln Ala Ala
                20                  25                  30

Leu Asn Arg Leu Leu Leu Glu Glu Ala
            35                  40

(2) INFORMATION FOR SEQ ID NO:3:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:3:

Ser Gln Glu Pro Pro Ile Ser Leu Asp Leu Thr Phe His Leu Leu Arg
1               5                   10                  15

Glu Met Leu His Met Ala Lys Ala Glu Gln Glu Ala Glu Gln Ala Ala
                20                  25                  30

Leu Asn Arg Asn Leu Leu Glu Glu Ala
            35                  40

(2) INFORMATION FOR SEQ ID NO:4:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:4:

```
Ser Gln Glu Pro Pro Ile Ser Leu Asp Leu Thr Phe His Leu Leu Arg
1               5                   10                  15
Glu Met Leu His Met Ala Lys Ala Glu Gly Glu Ala Glu Gln Ala Ala
                20                  25                  30
Leu Asn Arg Leu Leu Leu Glu Glu Ala
            35                  40
```

(2) INFORMATION FOR SEQ ID NO:5:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:5:

```
Ser Glu Glu Pro Pro Ile Ser Leu Asp Leu Thr Phe His Leu Leu Arg
1               5                   10                  15
Glu Val Leu His Xaa Ala Arg Ala Glu Gln Leu Ala Gln Gln Ala His
                20                  25                  30
Ser Asn Arg Lys Leu Leu Glu Ile Ile
            35                  40
```

(2) INFORMATION FOR SEQ ID NO:6:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:6:

Ser Glu Glu Pro Pro Ile Ser Leu Asp Leu Thr Phe His Leu Leu Arg
1               5                   10                  15

Glu Val Leu His Met Ala Arg Ala Glu Gln Leu Ala Gln Gln Ala His
                20                  25                  30

Ser Asn Arg Lys Leu Met Glu Ile Ile
        35                  40

(2) INFORMATION FOR SEQ ID NO:7:

(i) SEQUENCE CHARACTERISTICS:
      (A) LENGTH: 39 amino acids
      (B) TYPE: amino acid
      (D) TOPOLOGY: linear (ii) MOLECULE TYPE: peptide (xi) SEQUENCE DESCRIPTION: SEQ ID NO:7:

Glu Pro Pro Ile Ser Leu Asp Leu Thr Phe His Leu Leu Arg Glu Val
1               5                   10                  15

Leu Glu Met Ala Arg Ala Glu Gln Leu Ala Gln Gln Ala His Ile Asn
                20                  25                  30

Arg Asn Leu Met Glu Glu Ile
        35

(2) INFORMATION FOR SEQ ID NO:8:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:8:

Ser Glu Glu Pro Pro Ile Ser Leu Asp Leu Thr Phe His Leu Leu Arg
1               5                   10                  15

Glu Val Leu His Met Ala Arg Ala Glu Gly Leu Ala Gln Gln Ala His
                20                  25                  30

Ser Asn Arg Lys Leu Met Glu Ile Ile
        35                  40

(2) INFORMATION FOR SEQ ID NO:9:

(i) SEQUENCE CHARACTERISTICS:
       (A) LENGTH: 41 amino acids
       (B) TYPE: amino acid
       (D) TOPOLOGY: linear
   (ii) MOLECULE TYPE: peptide (xi) SEQUENCE DESCRIPTION: SEQ ID NO:9:

Ser Glu Glu Pro Pro Ile Ser Leu Asp Leu Thr Phe His Met Leu Arg
   1               5                   10                  15

Glu Val Leu Glu Arg Ala Arg Met Glu Gln Leu Ala Gln Gln Ala His
                   20                  25                  30

Ser Asn Arg Lys Leu Met Glu Ile Ile
                   35                  40

(2) INFORMATION FOR SEQ ID NO:10:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:10:

Ser Glu Glu Pro Pro Ile Ser Leu Glu Leu Thr Phe His Leu Leu Arg
   1               5                   10                  15

Glu Val Leu His Xaa Ala Arg Ala Glu Gln Leu Ala Glu Gln Ala His
                   20                  25                  30

Ile Asn Arg Lys Leu Met Glu Ile Ile
                   35                  40

(2) INFORMATION FOR SEQ ID NO:11:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:11:

Ser Glu Glu Pro Pro Ile Ser Xaa Asp Leu Ser Phe His Leu Leu Arg
1               5                   10                  15

Glu Val Leu Glu Met Ala Arg Ala Glu Gly Leu Ala Gln Gln Ala Leu
            20                  25                  30

Ser Asn Arg Lys Leu Met Glu Glu Ile
        35                  40

(2) INFORMATION FOR SEQ ID NO:12:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:12:

Ser Glu Glu Pro Pro Ile Ser Leu Asp Leu Thr Phe His Leu Leu Arg
1               5                   10                  15

Glu Val Leu Glu Xaa Ala Xaa Ala Glu Gln Leu Ala Gln Gln Ala His
            20                  25                  30

Ser Asn Arg Asn Leu Met Glu Glu Xaa
        35                  40

(2) INFORMATION FOR SEQ ID NO:13:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:13:

Ser Gln Glu Pro Pro Ile Ser Leu Asp Leu Thr Phe His Leu Leu Arg
1               5                   10                  15

Glu Val Leu Glu Met Ala Xaa Ala Glu Gly Leu Ala Glu Gln Ala His
            20                  25                  30

Ser Asn Arg Lys Leu Leu Glu Ile Ile
        35                  40

(2) INFORMATION FOR SEQ ID NO:14:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:14:

Ser Glu Glu Pro Pro Ile Ser Leu Asp Leu Thr Phe His Leu Leu Arg
   1               5                   10                  15

Glu Val Leu His Xaa Ala Arg Ala Glu Gln Leu Ala Gln Gln Ala Leu
               20                  25                  30

Ile Asn Arg Lys Leu Met Glu Glu Ile
               35                  40

(2) INFORMATION FOR SEQ ID NO:15:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:15:

Ser Glu Glu Pro Pro Ile Ser Leu Asp Leu Thr Phe His Leu Leu Arg
   1               5                   10                  15

Glu Val Leu His Arg Ala Arg Ala Glu Gln Leu Ala Gln Gln Ala Leu
               20                  25                  30

Ile Asn Arg Lys Leu Met Glu Ile Ile
               35                  40

(2) INFORMATION FOR SEQ ID NO:16:

(i) SEQUENCE CHARACTERISTICS:
       (A) LENGTH: 40 amino acids
       (B) TYPE: amino acid
       (D) TOPOLOGY: linear (ii) MOLECULE TYPE: peptide (xi) SEQUENCE DESCRIPTION: SEQ ID NO:16:

Xaa Gly Pro Pro Ile Ser Ile Asp Leu Ser Leu Glu Leu Leu Arg Lys
1               5                   10                  15

Met Ile His Ala Arg Lys Gln Glu Lys Glu Gln Ala Ala Asn
            20                  25                  30

Asn Arg Leu Leu Leu Asp Ile Ile
            35              40

(2) INFORMATION FOR SEQ ID NO:17:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:17:

Ser Gln Glu Pro Pro Ile Ser Leu Asp Leu Thr Phe His Leu Leu Arg
1               5                   10                  15

Glu Met Leu His Arg Ala Lys Ala Glu Gly Glu Ala Glu Gln Ala Ala
            20                  25                  30

Leu Asn Arg Leu Leu Leu Glu Glu Ala
            35              40

(2) INFORMATION FOR SEQ ID NO:18:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:18:

Ser Gln Glu Pro Pro Ile Ser Leu Glu Leu Thr Phe His Leu Leu Arg
1               5                   10                  15

Glu Xaa Leu His Arg Ala Lys Ala Glu Gln Glu Ala Glu Gln Ala Ala
            20                  25                  30

Leu Asn Arg Leu Leu Leu Glu Glu Ala
            35              40

(2) INFORMATION FOR SEQ ID NO:19:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:19:

Ser Gln Glu Pro Pro Ile Ser Leu Asp Leu Thr Phe His Leu Leu Arg
   1               5                   10                  15

Glu Xaa Leu His Xaa Ala Lys Ala Glu Gln Glu Ala Glu Gln Ala Ala
                   20                  25                  30

Leu Asn Arg Leu Leu Leu Glu Glu Ala
               35                  40

(2) INFORMATION FOR SEQ ID NO:20:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:20:

Ser Glu Glu Pro Pro Ile Ser Leu Asp Leu Thr Leu Glu Met Leu Arg
   1               5                   10                  15

Glu Met Leu Glu Met Glu Xaa Met Glu Lys Glu Ala Glu Gln Ala Ala
                   20                  25                  30

Leu Asn Arg Leu Leu Leu Glu Glu Ala
               35                  40

(2) INFORMATION FOR SEQ ID NO:21:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:21:

Ser Gln Glu Pro Pro Ile Ser Leu Asp Leu Thr Phe His Met Leu Arg
1               5                   10                  15

Glu Met Leu His Arg Ala Lys Met Glu Gly Glu Ala Glu Gln Ala Leu
            20                  25                  30

Ile Asn Arg Asn Leu Leu Glu Glu Ala
        35                  40

(2) INFORMATION FOR SEQ ID NO:22:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:22:

Ser Gln Glu Pro Pro Ile Ser Leu Asp Leu Thr Leu Glu Leu Leu Arg
1               5                   10                  15

Glu Met Leu Glu Arg Ala Lys Ala Glu Gln Glu Ala Glu Gln Ala Ala
            20                  25                  30

Leu Asn Arg Asn Tyr Leu Glu Glu Ala
        35                  40

(2) INFORMATION FOR SEQ ID NO:23:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:23:

Ser Gln Glu Pro Pro Ile Ser Leu Asp Leu Thr Phe His Leu Leu Arg
1               5                   10                  15

Glu Met Leu Glu Met Ala Lys Ala Glu Gln Leu Ala Glu Gln Ala Ala
            20                  25                  30

Leu Asn Arg Asn Leu Leu Glu Glu Ala
        35                  40

(2) INFORMATION FOR SEQ ID NO:24:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:24:

```
Ser Gln Glu Pro Pro Ile Ser Leu Asp Leu Thr Phe His Leu Leu Arg
1               5                   10                  15
Glu Met Leu His Met Ala Lys Ala Glu Gln Leu Ala Glu Gln Ala Ala
            20                  25                  30
Leu Asn Arg Leu Leu Leu Glu Glu Ala
            35                  40
```

(2) INFORMATION FOR SEQ ID NO:25:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:25:

```
Pro Pro Ile Ser Leu Asp Leu Thr Leu His Leu Leu Arg Glu Met Leu
1               5                   10                  15
Glu Met Glu Xaa Ala Glu Gln Glu Ala Glu Gln Ala Ala Leu Asn Arg
            20                  25                  30
Asn Leu Leu Glu Glu Ala
            35
```

(2) INFORMATION FOR SEQ ID NO:26:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:26:

Ser Gln Glu Pro Pro Ile Ser Leu Asp Leu Thr Phe His Leu Leu Arg
1               5                   10                  15

Glu Val Leu His Met Thr Lys Ala Asp Gln Leu Ala Gln Gln Ala His
            20                  25                  30

Ser Asn Arg Asn Leu Leu Asp Ile Ala
    35                  40

(2) INFORMATION FOR SEQ ID NO:27:
    (i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:27:

Ser Gln Glu Pro Pro Ile Ser Leu Asp Leu Thr Phe His Leu Leu Arg
1               5                   10                  15

Glu Val Leu His Xaa Thr Lys Ala Asp Gln Leu Ala Gln Gln Ala His
            20                  25                  30

Ser Asn Arg Lys Leu Leu Asp Ile Ala
    35                  40

(2) INFORMATION FOR SEQ ID NO:28:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:28:

Ser Gln Glu Pro Pro Ile Ser Leu Asp Leu Thr Phe His Leu Leu Arg
1               5                   10                  15

Glu Xaa Leu Glu Xaa Thr Lys Ala Asp Gln Leu Ala Gln Gln Ala His
            20                  25                  30

Ser Asn Arg Asn Leu Leu Asp Ile Ala
    35                  40

(2) INFORMATION FOR SEQ ID NO:29:

(i) SEQUENCE CHARACTERISTICS:
      (A) LENGTH: 39 amino acids
      (B) TYPE: amino acid
      (D) TOPOLOGY: linear (ii) MOLECULE TYPE: peptide (xi) SEQUENCE DESCRIPTION: SEQ ID NO:29:

Glu Pro Pro Ile Ser Leu Asp Leu Thr Phe His Met Leu Arg Glu Val
   1               5                   10                  15

Leu Glu Met Thr Lys Met Asp Gln Leu Ala Gln Gln Ala His Xaa Asn
                   20                  25                  30

Arg Lys Leu Leu Asp Ile Ala
                   35

(2) INFORMATION FOR SEQ ID NO:30:

(i) SEQUENCE CHARACTERISTICS:
      (A) LENGTH: 40 amino acids
      (B) TYPE: amino acid
      (D) TOPOLOGY: linear (ii) MOLECULE TYPE: peptide (xi) SEQUENCE DESCRIPTION: SEQ ID NO:30:

Gln Glu Pro Pro Ile Ser Leu Asp Leu Thr Phe His Leu Leu Arg Glu
   1               5                   10                  15

Xaa Leu Glu Met Thr Lys Ala Asp Gly Leu Ala Gln Gln Ala His Ser
                   20                  25                  30

Asn Arg Asn Leu Leu Asp Glu Ala
                   35                  40

(2) INFORMATION FOR SEQ ID NO:31:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:31:

Ser Glu Glu Pro Pro Ile Ser Leu Asp Leu Thr Phe His Leu Leu Arg
1               5                   10                  15

Glu Val Leu Glu Arg Ala Arg Ala Glu Gln Leu Ala Gln Gln Ala His
                20                  25                  30

Ser Asn Arg Lys Leu Met Glu Ile Ile
            35              40

(2) INFORMATION FOR SEQ ID NO:32:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:32:

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
                20                  25                  30

Ser Asn Arg Asn Leu Met Glu Ile Ile
            35              40

(2) INFORMATION FOR SEQ ID NO:33:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:33:

Ser Glu Glu Pro Pro Ile Ser Leu Asp Leu Thr Phe His Leu Leu Arg
1               5                   10                  15

Glu Val Leu Glu Met Ala Arg Ala Glu Gly Leu Ala Gln Gln Ala His
                20                  25                  30

Ser Asn Arg Lys Leu Met Glu Ile Ile
            35              40

(2) INFORMATION FOR SEQ ID NO:34:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:34:

Ser Glu Glu Pro Pro Ile Ser Leu Asp Leu Thr Phe His Leu Leu Arg
   1               5                   10                  15

Glu Val Leu Glu Met Ala Arg Ala Glu Gln Leu Ala Gln Gln Ala Leu
                   20                  25                  30

Ser Asn Arg Lys Leu Met Glu Ile Ile
                   35                  40

(2) INFORMATION FOR SEQ ID NO:35:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:35:

Ser Glu Glu Pro Pro Ile Ser Leu Asp Leu Thr Phe His Leu Leu Arg
   1               5                   10                  15

Glu Val Leu Glu Met Ala Arg Ala Glu Gln Leu Ala Gln Gln Ala His
                   20                  25                  30

Ile Asn Arg Lys Leu Met Glu Ile Ile
                   35                  40

(2) INFORMATION FOR SEQ ID NO:36:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:36:

Ser Glu Glu Pro Pro Ile Ser Leu Asp Leu Thr Phe His Leu Leu Arg
1               5                   10                  15

Glu Val Leu Glu Met Ala Arg Met Glu Gln Leu Ala Gln Gln Ala His
            20                  25                  30

Ser Asn Arg Lys Leu Met Glu Ile Ile
        35                  40

(2) INFORMATION FOR SEQ ID NO:37:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:37:

Ser Glu Glu Pro Pro Ile Ser Leu Asp Leu Thr Phe His Met Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

(2) INFORMATION FOR SEQ ID NO:38:

(i) SEQUENCE CHARACTERISTICS:
      (A) LENGTH: 38 amino acids
      (B) TYPE: amino acid
      (D) TOPOLOGY: linear (ii) MOLECULE TYPE: peptide (xi) SEQUENCE DESCRIPTION: SEQ ID NO:38:

Pro Pro Ile Ser Leu Asp Leu Thr Phe His Leu Leu Arg Glu Xaa Leu
1               5                   10                  15

His Xaa Ala Arg Ala Glu Gln Glu Ala Glu Gln Ala Leu Leu Asn Arg
            20                  25                  30

Asn Leu Leu Glu Glu Ala
        35

(2) INFORMATION FOR SEQ ID NO:39:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:39:

Ser Gln Glu Pro Pro Ile Ser Leu Asp Leu Thr Phe His Met Leu Arg
   1               5                   10                  15

Glu Met Leu His Met Ala Lys Met Glu Gln Glu Ala Glu Gln Ala Ala
                   20                  25                  30

Leu Asn Arg Leu Leu Leu Glu Glu Ala
                   35                  40

(2) INFORMATION FOR SEQ ID NO:40:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:40:

Ser Gln Glu Pro Pro Ile Ser Leu Asp Leu Thr Phe His Leu Leu Arg
   1               5                   10                  15

Glu Met Leu His Arg Ala Lys Ala Glu Gln Glu Ala Glu Gln Ala Ala
                   20                  25                  30

Ile Asn Arg Leu Leu Leu Glu Glu Ala
                   35                  40

CRF ANALOGS

This invention was made with Government support under Grant AM-26741 awarded by the National Institutes of Health (DHHS). The Government has certain rights in this invention.

This application is a continuation-in-part of application Ser. No. 209,537, filed Jun. 21, 1988, the disclosure of which is incorporated herein by reference.

This invention is directed to peptides and to methods for pharmaceutical treatment of mammals using such peptides. More specifically, the invention relates to analogs of the hentetracontapeptide CRF, to pharmaceutical compositions containing such CRF analogs and to methods of treatment of mammals using such CRF analogs.

BACKGROUND OF THE INVENTION

Experimental and clinical observations have supported the concept that the hypothalamus plays a key role in the regulation of adenohypophysial corticotropic cells secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. None of the secretagogs characterized met the criteria expected of a physiologic corticotropin releasing factor (CRF) until ovine CRF (oCRF) was characterized in 1981. The formula of 41-residue peptide is disclosed in U.S. Pat. No. 4,415,558.

Sauvagine is a 40-residue, amidated generally similar peptide which was isolated from the skin of the South American frog *Phyllomedusa sauvagei*. It was characterized by Erspamer et al. and was described in *Regulatory Peptides*, Vol. 2 (1981), pp. 1–13, wherein its formula is disclosed. Sauvagine and oCRF have been reported to have biological activity in lowering blood pressure in mammals and in stimulating the secretion of ACTH and β-endorphin.

Rat CRF(rCRF) has been isolated, purified and characterized as a hentetracontapeptide; its formula is disclosed in U.S. Pat. No. 4,489,163. It may alternatively be referred to as rat Amunine. The formula of human CRF has now been determined to be the same as that of rCRF. Synthetic rCRF and oCRF stimulate ACTH and β-endorphin activities in vitro and in vivo and substantially lower blood pressure for an extended time period.

SUMMARY OF THE INVENTION

Analogs of this family of 41-residue CRF peptides, having at least substantially the same biological activity in the foregoing respects as the native peptides are provided by the inclusion of one or more of the following residues: Met in the 14-position, His in the 20-position, Arg in the 21-position, Met in the 24-position, Gly in the 26-position, Leu in the 32-position, Ile in the 33-position, and/or Asn in the 36-position.

Pharmaceutical compositions in accordance with the invention include such CRF analogs, or nontoxic addition salts thereof, dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, β-endorphin, β-lipotropin, other products of the pro-opiomelanocortin gene and corticosterone and/or for the lowering of blood pressure and/or for affecting mood, behavioral and gastro-intestinal functions and autonomic nervous system activities. Furthermore CRF analogs may be used for the evaluation of the status of pituitary, cardiovascular, gastrointestinal or central nervous system functions.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser= L-serine, pGlu= L-pyroglutamic acid, Nle= L-norleucine, Nva= norvaline, Har= homoarginine, Orn= ornithine, etc. In addition the following abbreviations are used: CML= $C^\alpha CH_3$-L-leucine, and CMA= $C^\alpha CH_3$-L-alanine; by "des" is meant the residue in that position is deleted.

The invention provides analogs of CRF of the following formula (SEQ ID NO:1): Xaa-Xaa-Xaa-Xaa-Pro-Ile-Ser-Xaa-Xaa-Leu-Xaa-Xaa-Xaa-Xaa-Leu-Arg-Xaa-Xaa-Xaa-Xaa-Xaa-Xaa-Xaa-Xaa-Xaa-Xaa-Xaa-Xaa-Gln-Ala-Xaa-Xaa-Asn-Arg-Xaa-Xaa-Xaa-Xaa-Xaa-Xaa-Xaa-NH$_2$ wherein the N-terminus may be acylated by an acyl group having 7 or less carbon atoms; from 1 to 5 residues can be deleted in sequence beginning at the N-terminus; Xaa in the 1-position is Ser or D-Ser; Xaa in the 2-position is Glu, Gln, pGlu or D-pGlu; Xaa in the 3-position is Glu, Gly or D-Tyr; Xaa in the 4-position is Pro or D-Pro; Xaa in the 8- and 19-positions are selected from Leu, Ile, Ala, Gly, Val, Nle, Phe and Gln; Xaa in the 9-position is Asp or Glu; Xaa in the 11-position is Thr or Ser; Xaa in the 12-position is Phe, Leu, Ala, Ile, Gly, Val, Nle or Gln; Xaa in the 13-position is His, Tyr or Glu; Xaa in the 14-position is Leu or Met; Xaa in the 17-position is Glu or Lys; Xaa in the 18-position is Val, Nle or Met; Xaa in the 20-position is His or Glu; Xaa in the 21-position is Arg, Met, Nva, Ile, Ala, Leu, Nle, Val, Phe or Gln; Xaa in the 22-position is Ala, Thr, Asp or Glu; Xaa in the 23-position is Arg, Orn, Har or Lys; Xaa in the 24-position is Met, Leu, Ile, Ala, Gly, Val, Nle, Phe and Gln; Xaa in the 25-position is Glu or Asp; Xaa in the 26-position is Gly, Gln, Asn or Lys; Xaa in the 27-position is Leu, Ile, Ala, Val, Nva, Met, Nle, Phe, Asp, Asn, Gln or Glu; Xaa in the 28-position is Ala, Arg or Lys; Xaa in the 29-position is Gln or Glu; Xaa in the 32-position is Leu, His, Gly, Tyr or Ala; Xaa in the 33-position is Ile, Ser, Asn, Leu, Thr or Ala; Xaa in the 36-position is Asn, Lys, Orn, Arg, Har or Leu; Xaa in the 37-position is Leu or Tyr; Xaa in the 38-position is Met or Leu; Xaa in the 39-position is Glu or Asp; Xaa in the 40-position is Ile, Thr, Glu, Ala, Val, Leu, Nle, Phe, Nva, Gly, Asn or Gln; Xaa in the 41-position is Ile, Ala, Gly, Val, Leu, Nle, Phe, Gln or des; and the C-terminus is amidated, provided however that one or more of the following residues is present: Met in the 14-position, His in the 20-position, Arg in the 21-position, Met in the 24-position, Gly in the 26-position, Leu in the 32-position, Ile in the 33-position, and Asn in the 36-position. In any peptide where Ala appears, CMA can alternatively be used; for Leu in the 8, 10, 12, 14, 15, 19, 21, 24, 27 or 40-position, CML can alternatively be used. Nontoxic addition salts of these peptides are considered equivalents. At least one and preferably at least two of the following substituents are present in these peptides: His in the 20-position, Arg in the 21-position, Gly in the 26-position, and/or Asn in the 36-position. Most preferably, the residue His in the 20-position is one of two such substituents.

These analogs are considered to be at least as potent as native CRF, and certain preferred analogs include residues having a high alpha-helical forming potential particularly: Xaa in the 1-position is Ser, Xaa in the 2-position is Gln or Glu, Xaa in the 3-position is Glu, Xaa in the 4- and 5-position is Pro, Xaa in the 8-position is Leu, Xaa in the 11-position is Thr, Xaa in the 12-position is Phe or Leu, Xaa in the 13-position is His or Glu, Xaa in the 17-position is Glu, Xaa in the 18- and 21-position is Met or Nle, Xaa in the 19- and 37-position is Leu, Xaa in the 22- and 41-position is Ala, Xaa in the 23-position is Lys, Xaa in the 24- and 28-position is Ala, Xaa in the 25- and 39-position is Glu, Xaa in the 26-position is Gln, Xaa in the 27-position is Glu or Leu, Xaa in the 29-position is Glu, Xaa in the 32-position is His or Ala, Xaa in the 33-position is Ser or Leu, Xaa in the 38-position is Leu, and Xaa in the 40-position is Ile or Glu. One analog which has been found to be particularly preferred is [His$^{20}$]-AHC (alpha-helical CRF) having the formula: Ser-Gln-Glu-Pro-Pro-Ile-Ser-Leu-Asp-Leu-Thr-Phe-His-Leu-Leu-Arg-Glu-Met-Leu-His-Met-Ala-Lys-Ala-Glu-Gln-Glu-Ala-Glu-Gln-Ala-Ala-Leu-Asn-Arg-Leu-Leu-Leu-Glu-Glu-Ala (SEQ ID NO:2) wherein the C-terminus is amidated. It remains potent even if slightly shortened at the N-terminus, i.e., by a sequence of up to about 5 residues.

Two other analogs which are particularly preferred are [His$^{20}$, Asn$^{36}$]-AHC and [His$^{20}$, Gly$^{26}$]-AHC, respectively having the formulas: Ser-Gln-Glu-Pro-Pro-Ile-Ser-Leu-Asp-Leu-Thr-Phe-His-Leu-Leu-Arg-Clu-Met-Leu-His-Met-Ala-Lys-Ala-Glu-Gln-Glu-Ala-Glu-Cln-Ala-Ala-Leu-Asn-Arg-Asn-Leu-Leu-Glu-Glu-Ala (SEQ ID NO:3) and Ser-Gln-Glu-Pro-Pro-Ile-Ser-Leu-Asp-Leu-Thr-Phe-His-Leu-Leu-Arg-Glu-Met-Leu-His-Met-Ala-Lys-Ala-Glu-Cly-Glu-Ala-Glu-Gln-Ala-Ala-Leu-Asn-Arg-Leu-Leu-Leu-Clu-Glu-Ala (SEQ ID NO:4); the C-terminus of each being amidated.

Also preferred are [Met$^{14}$]-rCRF, [His$^{20}$]-rCRF, [Arg$^{21}$]-rCRF, [Met$^{24}$]-rCRF, [Gly$^{20}$]-rCRF, [Leu$^{32}$]-rCRF, [Ile$^{33}$]-rCRF, [Asn$^{36}$]-rCRF, [Met$^{14}$]-oCRF, [His$^{20}$]-oCRF, [Arg$^{21}$]-oCRF, [Met$^{24}$]-oCRF, [Gly$^{26}$]-oCRF, [Leu$^{32}$]-oCRF, [Ile$^{33}$]-oCRF and [Asn$^{36}$]-oCRF. Additional compounds that are especially preferred are: [His$^{20}$, Nle$^{21}$]-oCRF, [His$^{20}$, Nle$^{21}$]-rCRF, [His$^{20}$, Leu$^{38}$]-rCRF and [His$^{20}$, Nle$^{21}$, Leu$^{38}$]-rCRF which has the following sequence: Ser-Glu-Glu-Pro-Pro-Ile-Ser-Leu-Asp-Leu-Thr-Phe-His-Leu-Leu-Arg-Glu-Val-Leu-His-Xaa-Ala-Arg-Ala-Glu-Gln-Leu-Ala-Gln-Gln-Ala-His-Ser-Asn-Arg-Lys-Leu-Leu-Glu-Ile-Ile (SEQ ID NO:5), wherein the C-terminus is amidated and Xaa is Nle.

The peptides are synthesized by a suitable method, such as by exclusively solid-phase techniques, by partial solid-phase techniques, by fragment condensation or by classical solution addition. Certain CRF analogs which do not include D-isomer residues or unnatural amino acid residues may also be synthesized by recently developed recombinant DNA techniques.

Synthesis by the use of recombinant DNA techniques, for purposes of this application, should be understood to include the suitable employment of a structural gene coding for the desired form of CRF analog. Such a synthetic CRF peptide may be obtained by transforming a microorganism using an expression vector including a promoter and operator together with such structural gene and causing such transformed microorganism to express the CRF analog peptide. A non-human animal may also be used to produce the CRF analog peptide by gene-farming, the general techniques of which are known to those skilled in the art. For example, microinjection of embryos as described in WO83/01783, published May 26, 1983, and WO82/04443, published Dec. 23, 1982, may be used. The synthetic CRF analog peptide is then suitably recovered from the animal by extraction from sera or the like.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Thus, chemical synthesis of such a peptide analog may result in the formation of an intermediate of the following formula wherein the positions where substitutions potentially occur are represented by "R" plus an appropriate subscript: $X^1$-$R_1(X^2)$-$R_2(X^4$ or $X^5)$-$R_3(X^5$ or $X)$-$R_4$-Pro-Ile-Ser($X^2$)-$R_8$-$R_9(X^5)$-Leu-$R_{11}(X^2)$-$R_{12}(X^4)$-$R_{13}(X$ or $X^5)$-$R_{14}$-Leu-Arg($X^3$)-$R_1(X^5$ or $X^6)$-$R_{18}$-$R_{19}(X^4)$-$R_{20}(X^5$ or $X)$-$R_{21}(X^3)$-$R_{22}(X^2$ or $X^5)$-$R_{23}(X^3$ or $X^6)$-$R_{24}(X^4)$-$R_{25}(X^5)$-$R_{26}(X^4$ or $X^6)$-$R_{27}(X^4$ or $X^5)$-$R_{28}(X^3$ or $X^6)$-$R_{29}(X^4$ or $X^5)$-Gln($X^4$)-Ala-$R_{32}(X)$-$R_{33}(X^2$ or $X^4)$-Asn($X^4$)-Arg($X^3$)-$R_{36}(X^6$ or $X^4)$-$R_{37}(X)$-$R_{38}$-$R_{39}(X^5)$-$R_{40}(X^2$ or $X^4$ or $X^5)$-$R_{41}(X^4)$-$X^7$ wherein: the R-groups are as hereinbefore defined.

$X^1$ is either hydrogen or an α-amino protecting group. The α-amino protecting groups contemplated by $X^1$ are those known to be useful in the art in the stepwise synthesis of polypeptides. Among the classes of α-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenylmethyloxycarbonyl(FMOC), cyclopentyloxycarbonyl, adamantyloxycarbonyl, and cyclohexyloxycarbonyl; and (5) thiourethan-type protecting groups, such as phenylthiocarbonyl. The preferred α-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

$X^5$ is hydrogen or a protecting group, preferably xanthyl(Xan), for the amido group of Asn or Gln.

$X^5$ is hydrogen or an ester-forming protecting group for the $\beta$- or $\gamma$-carboxyl group of Asp or Glu, preferably selected from the class consisting of benzyl, 2,6-dichlorobenzyl, methyl, ethyl, cyclohexyl (OChx) and t-butyl ester. OBzl and CHe are most preferred.

$X^6$ is hydrogen or a protecting group for the side chain amino substituent of Lys or Orn. Illustrative of suitable side chain amino protecting groups are Z, 2-chlorobenzyloxycarbonyl(2-Cl-Z), Tos, t-amyloxy-carbonyl(Aoc), BOC and aromatic or aliphatic urethan-type protecting groups as specified hereinbefore.

When His is present, X is hydrogen or a protecting group for the imidazole nitrogen such as Tos or 2,4-dinitrophenyl(DNP), and when Tyr is present, X is hydrogen or a protecting group for the hydroxyl group such as DCB. When Met is present, the sulfur may be protected, if desired, with oxygen.

The selection of a side chain amino protecting group is not critical except that it should must be one which is not removed during deprotection of the $\alpha$-amino groups during the synthesis. Hence, the $\alpha$-amino protecting group and the side chain amino protecting group cannot be the same.

$X^7$ is NH$_2$, a protecting group such as an ester or an anchoring bond used in solid phase synthesis for linking to a solid resin support, preferably one represented by the formulae: —NH-benzhydrylamine (BHA) resin support and —NH-paramethylbenzhydrylamine (MBHA) resin support. Cleavage from a BHA or MBHA resin directly gives the CRF analog amide. By employing a methyl-derivative of such a resin, a methyl-substituted amide can be created which is considered to be the equivalent of the unsubstituted amide.

In the formula for the intermediate, at least one of X, $X^1$, $X^2$, $X^3$, $X^4$, $X^5$ and $X^6$ is a protecting group. The particular amino acid chosen for each the R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the $\alpha$-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the optional acyl group at the N-terminus, acetyl, formyl, acrylyl and benzoyl are preferred. For the 1 to 10 amino acid peptide which may be optionally included without adversely affecting the potency, any amino acids may be used, but the L- or D- forms cf the naturally occurring amino acids would normally be used. Moreover, as indicated hereinbefore, the N-terminus can be slightly shortened without significantly affecting biological potency.

The present invention may also be considered to provide a process for the manufacture of compounds comprising the steps of (a) forming an intermediate peptide having at least one protective group and having the aforementioned formula wherein: X, $X^1$, $X^2$, $X^3$, $X^4$, $X^5$ and $X^6$ are each either hydrogen or a protective group, and $X^7$ is either a protective group or an anchoring bond to resin support or NH$_2$ and (b) splitting off the protective group or groups or anchoring bond from said intermediate peptide and (c) if desired, converting a resulting peptide into a nontoxic addition salt thereof.

When the peptides are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is usually commenced from the C-terminus end of the peptide by coupling a protected $\alpha$-amino acid to a suitable resin as generally set forth in U.S. Pat. No. 4,244,946 issued Jan. 21, 1981 to Rivier et al., the disclosure of which is incorporated herein by reference. Such a starting material for rCRF analogs can be prepared by attaching $\alpha$-amino-protected Ile to a BHA resin.

Ile protected by BOC is coupled to the BHA resin using methylene chloride and dimethylformamide (DMF). Following the coupling of BOC-Ile to the resin support, the $\alpha$-amino protecting group is removed, as by using trifluoroacetic acid(TFA) in methylene chloride, TFA alone or with HCl in dioxane. Preferably 50 volume % TFA in methylene chloride is used with 0-5 weight % 1,2 ethanedithiol. The deprotection is carried out at a temperature between about 0° C. and room temperature. Other standard cleaving reagents and conditions for removal of specific $\alpha$-amino protecting groups may be used as described in Schroder & Lubke, "The Peptides", 1, pp 72-75 (Academic Press 1965).

After removal of the $\alpha$-amino protecting group of Ile, the remaining $\alpha$-amino- and side chain-protected amino acids are coupled stepwise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCCI) and N,N'-diisopropyl carbodiimide(DICI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1-27 (1970).

Each protected amino acid or amino acid sequence is introduced into the solid phase reactor in about a four-fold excess, and the coupling is carried out in a medium of dimethylformamide(DMF):CH$_2$Cl$_2$ (1:1) or in DMF or CH$_2$Cl$_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp.1927-1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups X, $X^1$, $X^2$, $X^3$, $X^4$, $X^5$ and $X^6$ and the α-amino protecting group $X^1$ (unless it is an acyl group which is intended to be present in the final peptide), to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate potential S-alkylation.

The following Example sets forth the preferred method for synthesizing CRF analogs by the solid-phase technique.

EXAMPLE I

The synthesis of [AcPro[4], His[20], Nle[21], Leu[38]]-rCRF(4-41) is conducted in a stepwise manner on a MBHA hydrochloride resin, such as available from Bachem, Inc., having a substitution range of about 0.1 to 0.5 mmoles/gm. resin. This compound has the sequence of SEQ ID NO:5: Ser-Glu-Glu-Pro-Pro-Ile-Ser-Leu-Asp-Leu-Thr-Phe-His-Leu-Leu-Arg-Glu-Val-Leu-His-Xaa-Ala-Arg-Ala-Glu-Gln-Leu-Ala-Gln-Gln-Ala-His-Ser-Asn-Arg-Lys-Leu-Leu-Glu-Ile-Ile, wherein the N-terminus is shortened by 3 residues and acetylated, the C-terminus is amidated and Xaa is Nle. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | CH₂Cl₂ wash-80 ml. (2 times) | 3 |
| 2 | Methanol(MeOH) wash-30 ml. (2 times) | 3 |
| 3 | CH₂Cl₂ wash-80 ml. (3 times) | 3 |
| 4 | 50 percent TFA plus 5 percent 1,2-ethanedithiol in CH₂Cl₂-70 ml. (2 times) | 12 |
| 5 | Isopropanol wash-80 ml. (2 times) | 3 |
| 6 | TEA 12.5 percent in CH₂Cl₂-70 ml. (2 times) | 5 |
| 7 | MeOH wash-40 ml. (2 times) | 2 |
| 8 | CH₂Cl₂ wash-80 ml. (3 times) | 3 |
| 9 | Boc-amino acid (10 mmoles) in 30 ml. of either DMF or CH₂Cl₂, depending upon the solubility of the particular protected amino acid, (1 time) plus DCCI (10 mmoles) in CH₂Cl₂ | 30-300 |

Coupling of BOC-Ile results in the substitution of about 0.35 mmol. Ile per gram of resin. All solvents that are used are preferably degassed, preferably by sparging with an inert gas, e.g. helium or nitrogen.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) can be used to activate the carboxyl end of Asn or Gln, and for example, BOC-Asn(ONp) can be coupled overnight using one equivalent of N-hydroxy benzotriazole (HOBt) in a 50% mixture of DMF and methylene chloride. The amido group of Asn or Gln is usually protected by Xan when DCCI coupling is used instead of the active ester method. BOC-Asn and BOC-Glu are preferably coupled with the amido group unprotected in the presence of 2 equivalents of HOBt. 2-Cl-Z is used as the protecting group for the Lys side chain. Tos is used to protect the guanidino group of Arg and the imidazole group of His, and the side chain carboxyl groups of Glu or Asp are protected as the cyclohexyl esters (OChx). At the end of the synthesis, the following composition is obtained: BOC-Pro-Pro-Ile-Ser(Bzl)-Leu-Asp (β-OChx)-Leu-Thr(Bzl)-Phe-His(Tos)-Leu-Leu-Arg(Tos)-Glu(γ-OChx)-Val-Leu-His(Tos)-Nle-Ala-Arg(Tos)-Ala-Glu (γ-OChx)-Gln-Leu-Ala-Gln-Gln-Ala-His(Tos)-Ser(Bzl)-Asn-Arg(Tos)-Lys(2-Cl-Z)-Leu-Leu-Glu(γ-OChx)-Ile-Ile-resin support. The peptide resin is then divided into two halves, and one-half is treated with TFA to deblock the α-amino protecting group. It is then reacted with acetic anhydride to acetylate the N-terminal Pro-residue.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0° C. for one hour. After elimination of the HF under high vacuum, the resin-peptide is washed with dry diethyl ether, and the peptide is then extracted with de-gassed 2N aqueous acetic acid and separated from the resin by filtration.

The peptide is purified by semi-preparative HPLC as described in Rivier et al., *Peptides: Structure and Biological Function* (1979) pp. 125-128, and Rivier et al., *J. Chromatography* (1983). The chromatographic fractions are carefully monitored by HPLC, and only the fractions showing substantial purity were pooled.

To check whether the precise sequence was achieved, the rCRF analog is hydrolyzed in sealed evacuated tubes containing 4 N methanesulfonic acid, 3 μl of thioglycol/ml. and 1 nmol of Nle (as an internal standard) for 20 hours at 110° C. Amino acid analyses of the hydrolysates using a Beckman 121 MB amino acid analyzer show the following amino acid ratios: Asx(1.93), Thr(0.93), Ser(1.91), Glx(6.14), Pro(1.88), Ala(4.00), Val(0.90), Nle(1.12), Ile(1.97), Leu(8.23), Phe(0.86), Lys(1.07), His(2.82) and Arg(2.83), with all values being normalized to Ala. This confirms that the desired 38-residue peptide structure was obtained. The value for Ile is expected to be substantially below 3 as a result of the very slow hydrolysis of the Ile-Ile bond at the C-terminus, causing this dipeptide to show up as only a single residue.

Specific optical rotation of the peptide, which was synthesized and purified in the foregoing manner, was measured on a Perkin Elmer Model 141 optical polarimeter as $[\alpha]_D^{22°} = -66° \pm 1.0$ (c=1 in 1% acetic acid) (without correcting for the presence of H₂O and TFA). It was also calculated to have a purity of greater than 95%.

The other one-half of the peptide-resin is then further treated to add the 3 residues Glu. Glu and Ser at the N-terminus to create the 41-residue peptide intermediate. It is then deprotected and purified as described above to produce the peptide [His$^{20}$, Nle$^{21}$, Leu$^{38}$]-rCRF.

The synthetic peptides from Example I and synthetic oCRF are examined for their effects on the secretion of ACTH and β-endorphin in vitro and also in vivo. The potency of synthetic oCRF to stimulate the secretion of ACTH and β-endorphin by cultured rat pituitary cells is measured using the procedure as generally set forth in *Endocrinology*, 91, 562 (1972). Half-maximal responses are observed at concentrations of the two peptides which are less than the synthetic oCRF concentration of about 250 picomolar which is needed to achieve such a response. In vivo testing using the general procedure set forth in C. Rivier et al., *Science*, 218, 377 (1982), shows good biological potency for the peptides.

EXAMPLE II

The synthetic peptide [His$^{20}$]-rCRF having the formula: Ser-Glu-Glu-Pro-Pro-Ile-Ser-Leu-Asp-Leu-Thr-Phe-His-Leu-Leu-Arg-Glu-Val-Leu-His-Met-Ala-Arg-Ala-Glu-Gln-Leu-Ala-Gln-Gln-Ala-His-Ser-Asn-Arg-Lys-Leu-Met-Glu-Ile-Ile (SEQ ID NO:6), wherein the C-terminus is amidated, is synthesized using a procedure generally as set forth in Example I. The peptide is purified in the manner set forth in Example I.

This peptide is likewise considered to stimulate the secretion of ACTH and β-END-LI and to cause a very significant lowering of blood pressure.

EXAMPLE III

The synthetic peptide [His$^{20}$]-AHC (SEQ ID NO:2) having the formula: Ser-Gln-Glu-Pro-Pro-Ile-Ser-Leu-Asp-Leu-Thr-Phe-His-Leu-Leu-Arg-Glu-Met-Leu-His-Met-Ala-Lys-Ala-Glu-Gln-Glu-Ala-Glu-Gln-Ala-Ala-Leu-Asn-Arg-Leu-Leu-Leu-Glu-Glu-Ala, wherein the C-terminus is amidated, is synthesized using a procedure generally as set forth in Example I. This peptide is likewise considered to stimulate the secretion of ACTH and β-END-LI and to cause a very significant lowering of blood pressure.

EXAMPLE IV

The peptide [des Ser$^1$-Glu$^2$, Ile$^{33}$, Asn$^{36}$]-rCRF having the formula: Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ile-Asn-Arg-Asn-Leu-Met-Glu-Glu-Ile (SEQ ID NO:7), wherein the C-terminus is amidated, is synthesized. This peptide is likewise considered to stimulate the secretion of ACTH and β-END-LI and to cause a very significant lowering of blood pressure.

EXAMPLE V

The peptide [His$^{20}$, Gly$^{26}$]-rCRF having the formula: Ser-Glu-Glu-Pro-Pro-Ile-Ser-Leu-Asp-Leu-Thr-Phe-His-Leu-Leu-Arg-Glu-Val-Leu-His-Met-Ala-Arg-Ala-Glu-Gly-Leu-Ala-Gln-Gln-Ala-His-Ser-Asn-Arg-Lys-Leu-Met-Glu-Ile-Ile (SEQ ID NO:8), wherein the C-terminus is amidated, is synthesized. This peptide is likewise considered to stimulate the secretion of ACTH and β-END-LI and to cause a very significant lowering of blood pressure.

EXAMPLE VI

The peptide [Acetyl-Gly$^1$, Ile$^{33}$, Glu$^{40}$]-rCRF is synthesized. This peptide is likewise considered to stimulate the secretion of ACTH and β-END-LI and to cause a very significant lowering of blood pressure.

EXAMPLE VII

The peptide [Met$^{14,24}$, Arg$^{21}$]-rCRF having the formula: Ser-Glu-Glu-Pro-Pro-Ile-Ser-Leu-Asp-Leu-Thr-Phe-His-Met-Leu-Arg-Glu-Val-Leu-Glu-Arg-Ala-Arg-Met-Glu-Gln-Leu-Ala-Gln-Gln-Ala-His-Ser-Asn-Arg-Lys-Leu-Met-Glu-Ile-Ile (SEQ ID NO:9), wherein the C-terminus is amidated, is synthesized. This peptide is likewise considered to stimulate the secretion of ACTH and β-END-LI and to cause a very significant lowering of blood pressure.

EXAMPLE VIII

The peptide [Acrylyl-Val$^1$, Ser$^2$, Arg$^{21}$]-rCRF is synthesized. This peptide is likewise considered to stimulate the secretion of ACTH and β-END-LI and to cause a very significant lowering of blood pressure.

EXAMPLE IX

The peptide [Glu$^9$, His$^{20}$, Nle$^{21}$, Glu$^{29}$, Ile$^{33}$]-rCRF having the formula: Ser-Glu-Glu-Pro-Pro-Ile-Ser-Leu-Glu-Leu-Thr-Phe-His-Leu-Leu-Arg-Glu-Val-Leu-His-Xaa-Ala-Arg-Ala-Glu-Gln-Leu-Ala-Glu-Gln-Ala-His-Ile-Asn-Arg-Lys-Leu-Met-Glu-Ile-Ile (SEQ ID NO:10), wherein the C-terminus is amidated and Xaa is Nle, is synthesized. This peptide is likewise considered to stimulate the secretion of ACTH and β-END-LI and to cause a very significant lowering of blood pressure.

EXAMPLE X

The peptide [Benzoyl-Gly$^1$, Nle$^{12}$, His$^{20}$, Arg$^{30}$]-rCRF is synthesized. This peptide is likewise considered to stimulate the secretion of ACTH and β-END-LI and to cause a very significant lowering of blood pressure.

EXAMPLE XI

The peptide [Nle$^8$, Ser$^{11}$, Gly$^{26}$, Leu$^{32}$, Glu$^{40}$]-rCRF having the formula: Ser-Glu-Glu-Pro-Pro-Ile-Ser-Xaa-Asp-Leu-Ser-Phe-His- Leu-Leu-Arg-Glu-Val-Leu-Glu-Met-Ala-Arg-Ala-Glu-Gly-Leu-Ala-Gln-Gln-Ala-Leu-Ser-Asn-Arg-Lys-Leu-Met-Glu-Glu-Ile (SEQ ID NO:11), wherein the C-terminus is amidated and Xaa is Nle, is synthesized. This peptide is likewise considered to stimulate the secretion of ACTH and β-END-LI and to cause a very significant lowering of blood pressure.

EXAMPLE XII

The peptide [Nle$^{21}$, Har$^{23}$, Asn$^{36}$, Glu$^{40}$, Nle$^{41}$]-rCRF having the formula: Ser-Glu-Glu-Pro-Pro-Ile-Ser-Leu-Asp-Leu-Thr-Phe-His-Leu-Leu-Arg-Glu-Val-Leu-Glu-Xaa-Ala-Xaa-Ala-Glu-Gln-Leu-Ala-Gln-Gln-Ala-His-Ser-Asn-Arg-Asn-Leu-Met-Glu-Glu-Xaa (SEQ ID NO:12), wherein the C-terminus is amidated and Xaa in the 23-position is Har and Xaa in the 21- and 41-positions is Nle, is synthesized, is likewise considered to stimulate the secretion of ACTH and β-END-LI and to cause a very significant lowering of blood pressure.

EXAMPLE XIII

The peptide [Acetyl-Pro$^4$, His$^{20}$, Glu$^{29,40}$, Asn$^{36}$]-rCRF(4-41) is synthesized. This peptide is likewise considered to stimulate the secretion of ACTH and β-END-LI and to cause a very significant lowering of blood pressure.

EXAMPLE XIV

The peptide [Gln$^2$, Orn$^{23}$, Gly$^{26}$, Glu$^{29}$, Leu$^{38}$]-rCRF having the formula: Ser-Gln-Glu-Pro-Pro-Ile-Ser-Leu-Asp-Leu-Thr-Phe-His-Leu-Leu-Arg-Glu-Val-Leu-Glu-Met-Ala-Xaa-Ala-Glu-Gly-Leu-Ala-Glu-Gln-Ala-His-Ser-Asn-Arg-Lys-Leu-Leu-Glu-Ile-Ile (SEQ ID NO:13), wherein the C-terminus is amidated and Xaa is Orn, is synthesized. This peptide is likewise considered to stimulate the secretion of ACTH and β-END-LI and to cause a very significant lowering of blood pressure.

EXAMPLE XV

The peptide [His$^{20}$, Nle$^{21}$, Leu$^{32}$, Ile$^{33}$, Glu$^{40}$]-rCRF having the formula: Ser-Glu-Glu-Pro-Pro-Ile-Ser-Leu-Asp-Leu-Thr-Phe-His-Leu-Leu-Arg-Glu-Val-Leu-His-Xaa-Ala-Arg-Ala-Glu-Gln-Leu-Ala-Gln-Gln-Ala-Leu-Ile-Asn-Arg-Lys-Leu-Met-Glu-Glu-Ile (SEQ ID NO:14), wherein the C-terminus is amidated and Xaa is Nle, is synthesized. This peptide is likewise considered to stimulate the secretion of ACTH and β-END-LI and to cause a very significant lowering of blood pressure.

EXAMPLE XVI

The peptide [His$^{20}$, Arg$^{21}$, Leu$^{32}$, Ile$^{33}$]-rCRF having the formula: Ser-Glu-Glu-Pro-Pro-Ile-Ser-Leu-Asp-Leu-Thr-Phe-His-Leu-Leu-Arg-Glu-Val-Leu-His-Arg-Ala-Arg-Ala-Glu-Gln-Leu-Ala-Gln-Gln-Ala-Leu-Ile-Asn-Arg-Lys-Leu-Met-Glu-Ile-Ile (SEQ ID NO:15), wherein the C-terminus is amidated, is synthesized. This peptide is likewise considered to stimulate the secretion of ACTH and β-END-LI and to cause a very significant lowering of blood pressure.

EXAMPLE XVII

The peptide [His$^{19}$, Ala$^{20}$, Arg$^{21}$, Glu$^{28}$, Ile$^{39}$]-sauvagine having the formula: Xaa-Gly-Pro-Pro-Ile-Ser-Ile-Asp-Leu-Ser-Leu-Glu-Leu-Leu-Arg-Lys-Met-Ile-His-Ala-Arg-Lys-Gln-Glu-Lys-Glu-Lys-Glu-Gln-Ala-Ala-Asn-Asn-Arg-Leu-Leu-Leu-Asp-Ile-Ile (SEQ ID NO:16), wherein the C-terminus is amidated, and Xaa is pGlu, is synthesized. This peptide is likewise considered to stimulate the secretion of ACTH and β-END-LI and to cause a very significant lowering of blood pressure.

EXAMPLE XVIII

The synthetic peptide [His$^{20}$, Arg$^{21}$, Gly$^{26}$]-AHC having the formula: Ser-Gln-Glu-Pro-Pro-Ile-Ser-Leu-Asp-Leu-Thr-Phe-His- Leu-Leu-Arg-Glu-Met-Leu-His-Arg-Ala-Lys-Ala-Glu-Gly-Glu-Ala-Glu-Gln-Ala-Ala-Leu-Asn-Arg-Leu-Leu-Leu-Glu-Glu-Ala (SEQ ID NO:17), wherein the C-terminus is amidated, is synthesized using a procedure generally as set forth in Example I. This peptide is likewise considered to stimulate the secretion of ACTH and β-END-LI and to cause a very significant lowering of blood pressure.

EXAMPLE XIX

The peptide [Glu$^9$, Nle$^{18}$, His$^{20}$, Arg$^{21}$]-AHC having the formula: Ser-Gln-Glu-Pro-Pro-Ile-Ser-Leu-Glu-Leu-Thr-Phe-His-Leu-Leu-Arg-Glu-Xaa-Leu-His-Arg-Ala-Lys-Ala-Glu-Gln-Glu-Ala-Glu-Gln-Ala-Ala-Leu-Asn-Arg-Leu-Leu-Leu-Glu-Glu-Ala (SEQ ID NO:18), wherein the C-terminus is amidated, and Xaa is Nle, is synthesized. This peptide is likewise considered to stimulate the secretion of ACTH and β-END-LI and to cause a very significant lowering of blood pressure.

EXAMPLE XX

The peptide [Nle$^{18,21}$, His$^{20}$]-AHC having the formula: Ser-Gln-Glu-Pro-Pro-Ile-Ser-Leu-Asp-Leu-Thr-Phe-His-Leu-Leu-Arg-Glu-Xaa-Leu-His-Xaa-Ala-Lys-Ala-Glu-Gln-Glu-Ala-Glu-Gln-Ala-Ala-Leu-Asn-Arg-Leu-Leu-Leu-Glu-Glu-Ala (SEQ ID NO:19), wherein the C-terminus is amidated, and Xaa is Nle, is synthesized. This peptide is likewise considered to stimulate the secretion of ACTH and β-END-LI and to cause a very significant lowering of blood pressure.

EXAMPLE XXI

The peptide [D-Pro$^4$, Nle$^{18,21}$, Ile$^{33}$, Asn$^{36}$]-AHC having the formula: H-Ser-Gln-Glu-D-Pro-Pro-Ile-Ser-Leu-Asp-Leu-Thr-Phe-His-Leu-Leu-Arg-Glu-Nle-Leu-Glu-Nle-Ala-Lys-Ala-Glu-Gln-Glu-Ala-Glu-Gln-Ala-Ala-Ile-Asn-Arg-Asn-Leu-Leu- Glu-Glu-Ala-NH$_2$ is synthesized. This peptide is likewise considered to stimulate the secretion of ACTH and β-END-LI and to cause a very significant lowering of blood pressure.

EXAMPLE XXII

The peptide [D-Tyr$^3$, Nle$^{18,21}$, His$^{20}$, Gly$^{25}$]-AHC having the formula: H-Ser-Gln-D-Tyr-Pro-Pro-Ile-Ser-Leu-Asp-Leu-Thr-Phe-His-Leu-Leu-Arg-Glu-Nle-Leu-His-Nle-Ala-Lys-Ala-Gly-Gln-Glu-Ala-Glu-Gln-Ala-Ala-Leu-Asn-Arg-Leu-Leu-Leu-Glu-Glu-Ala-NH$_2$ is synthesized. This peptide is likewise considered to stimulate the secretion of ACTH and β-END-LI and to cause a very significant lowering of blood pressure.

EXAMPLE XXIII

The peptide [Gly$^{2,13,22}$, Leu$^{12}$, Met$^{14,24}$, Orn$^{23}$]-AHC having the formula: Ser-Gly-Glu-Pro-Pro-Ile-Ser-Leu-Asp-Leu-Thr-Leu-Glu-Met-Leu-Arg-Glu-Met-Leu-Glu-Met-Glu-Xaa-Met-Glu-Lys-Glu-Ala-Glu-Gln-Ala-Ala-Leu-Asn-Arg-Leu-Leu-Leu-Glu-Glu-Ala (SEQ ID NO:20), wherein the C-terminus is amidated, and Xaa is Orn, is synthesized. This peptide is likewise considered to stimulate the secretion of ACTH and β-END-LI and to cause a very significant lowering of blood pressure.

EXAMPLE XXIV

The synthetic peptide having the formula: Ser-Gln-Glu-Pro-Pro-Ile-Ser-Leu-Asp-Leu-Thr-Phe-His-Met-Leu-Arg-Glu-Met-Leu-His-Arg-Ala-Lys-Met-Glu-Gly-Glu-Ala-Glu-Gln-Ala-Leu-Ile-Asn-Arg-Asn-Leu-Leu-Glu-Glu-Ala (SEQ ID NO:21), wherein the C-terminus is amidated, is synthesized. This peptide is likewise considered to stimulate the secretion of ACTH and β-END-LI and to cause a very significant lowering of blood pressure.

EXAMPLE XXV

The peptide [Leu$^{12}$, Glu$^{13}$, Arg$^{21}$, Asn$^{36}$, Tyr$^{37}$]-AHC having the formula: Ser-Gln-Glu-Pro-Pro-Ile-Ser-Leu-Asp-Leu-Thr-Leu-Glu-Leu-Leu-Arg-Glu-Met-Leu-Gln-Arg-Ala-Lys-Ala-Glu-Gln-Glu-Ala-Glu-Gln-Ala-Ala-Leu-Asn-Arg-Asn-Tyr-Leu-Glu-Glu-Ala (SEQ ID NO:22), wherein the C-terminus is amidated, is synthesized. This peptide is likewise considered to stimulate the secretion of ACTH and β-END-LI and to cause a very significant lowering of blood pressure.

EXAMPLE XXVI

The peptide having the formula: Leu-Leu-Arg-Glu-Met-Leu-Glu-Met-Ala-Lys-Ala-Glu-Gln-Leu-Ala-Glu-Gln-Ala-Ala-Leu-Asn-Arg-Asn-Leu-Leu-Glu-Glu-Ala (SEQ ID NO:23), wherein the C-terminus is amidated, and the Leu residues in positions 10, 14, 19, 27, 33 and 38 each have a methyl substitution on the α-carbon atom, is synthesized. This peptide is likewise considered to stimulate the secretion of ACTH and β-END-LI and to cause a very significant lowering of blood pressure.

EXAMPLE XXVII

The peptide having the formula: Ser-Gln-Glu-Pro-Pro-Ile-Ser-Leu-Asp-Leu-Thr-Phe-His-Leu-Leu-Arg-Glu-Met-Leu-His-Met-Ala-Lys-Ala-Glu-Gln-Leu-Ala-Glu-Gln-Ala-Ala-Leu-Asn-Arg-Leu-Leu-Leu-Glu-Glu-Ala (SEQ ID NO:24), wherein the C-terminus is amidated, and the Leu residues in the 10, 15 and 37-positions and the Ala residues in the 22, 32 and 41-positions each have a methyl substitution on the α-carbon atom, is synthesized. This peptide is likewise considered to stimulate the secretion of ACTH and β-END-LI and to cause a very significant lowering of blood pressure.

EXAMPLE XXVIII

The peptide having the formula: H-D-Tyr-D-Pro-Pro-Ile-Ser-Leu-Asp-Leu-Thr-Phe-His-Leu-Leu-Arg-Glu-Nle-Leu-Glu-Arg-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized. This peptide is likewise considered to stimulate the secretion of ACTH and β-END-LI and to cause a very significant lowering of blood pressure.

EXAMPLE XXIX

The peptide having the formula: H-D-Pro-Pro-Ile-Ser-Leu-Asp-Leu-Thr-Phe-His-Leu-Leu-Arg-Glu-Nle-Leu-His-Nle-Ala-Lys-Ala-Glu-Gln-Glu-Ala-Glu-Gln-Ala-Ala-Ile-Asn-Arg-Leu-Leu-Leu-Glu-Glu-Ala-NH$_2$ is synthesized. This peptide is likewise considered to stimulate the secretion of ACTH and β-END-LI and to cause a very significant lowering of blood pressure.

EXAMPLE XXX

The peptide having the formula: Pro-Pro-Ile-Ser-Leu-Asp-Leu-Thr-Leu-His-Leu-Leu-Arg-Glu-Met-Leu-Glu-Met-Glu-Xaa-Ala-Glu-Gln-Glu-Ala-Glu-Gln-Ala-Ala-Leu-Asn-Arg-Asn-Leu-Leu-Glu-Glu-Ala (SEQ ID NO:25), wherein the C-terminus is amidated, and Xaa is Orn, is synthesized. This peptide is likewise considered to stimulate the secretion of ACTH and β-END-LI and to cause a very significant lowering of blood pressure.

EXAMPLE XXXI

The peptide [His$^{20}$, Asn$^{36}$]-oCRF having the formula: Ser-Gln-Glu-Pro-Pro-Ile-Ser-Leu-Asp-Leu-Thr-Phe-His-Leu-Leu-Arg-Glu-Val-Leu-His-Met-Thr-Lys-Ala-Asp-Gln-Leu-Ala-Gln-Gln-Ala-His-Ser-Asn-Arg-Asn-Leu-Leu-Asp-Ile-Ala (SEQ ID NO:26), wherein the C-terminus is amidated, is synthesized. This peptide is likewise considered to stimulate the secretion of ACTH and βEND-LI and to cause a very significant lowering of blood pressure.

EXAMPLE XXXII

The peptide [His$^{20}$, Nle$^{21}$]-oCRF having the formula: Ser-Gln-Glu-Pro-Pro-Ile-Ser-Leu-Asp-Leu-Thr-Phe-His-Leu-Leu-Arg-Glu-Val-Leu-His-Xaa-Thr-Lys-Ala-Asp-Gln-Leu-Ala-Gln-Gln-Ala-His-Ser-Asn-Arg-Lys-Leu-Leu-Asp-Ile-Ala (SEQ ID NO:27), wherein the C-terminus is amidated, and Xaa is Nle, is synthesized. This peptide is likewise considered to stimulate the secretion of ACTH and β-END-LI and to cause a very significant lowering of blood pressure.

EXAMPLE XXXIII

The peptide [Nle$^{18,21}$, Asn$^{36}$]-oCRF having the formula: Ser-Gln-Glu-Pro-Pro-Ile-Ser-Leu-Asp-Leu-Thr-Phe-His-Leu-Leu-Arg-Glu-Xaa-Leu-Glu-Xaa-Thr-Lys-Ala-Asp-Gln-Leu-Ala-Gln-Gln-Ala-His-Ser-Asn-Arg-Asn-Leu-Leu-Asp-Ile-Ala (SEQ ID NO:28), wherein the C-terminus is amidated, and Xaa is Nle, is synthesized. This peptide is likewise considered to stimulate the secretion of ACTH and β-END-LI and to cause a very significant: lowering of blood pressure.

EXAMPLE XXXIV

The peptide [D-Pro$^4$, His$^{20}$]-oCRF(4-41) having the formula: H-D-Pro-Ile-Ser-Leu-Asp-Leu-Thr-Phe-His-Leu-Leu-Arg-Glu-Val-Leu-His-Met-Thr-Lys-Ala-Asp-Gln-Leu-Ala-Gln-Gln-Ala-His-Ser-Asn-Arg-Lys-Leu-Leu-Asp-Ile-Ala-NH$_2$ is synthesized. This peptide is likewise considered to stimulate the secretion of ACTH and β-END-LI and to cause a very significant lowering of blood pressure.

EXAMPLE XXXV

The peptide [Met$^{14,24}$, CML$^{33}$]-oCRF(3-41) having the formula: Glu-Pro-Pro-Ile-Ser-Leu-Asp-Leu-Thr-Phe-His-Met-Leu-Arg-Glu-Val-Leu-Glu-Met-Thr-Lys-Met-Asp-Gln-Leu-Ala-Gln-Gln-Ala-His-Xaa-Asn-Arg-Lys-Leu-Leu-Asp-Ile-Ala-NH$_2$ (SEQ ID NO:29), wherein the C-terminus is amidated, and Xaa is CML, is synthesized. This peptide is likewise considered to stimulate the secretion of ACTH and β-END-LI and to cause a very significant lowering of blood pressure.

EXAMPLE XXXVI

The peptide [Nle$^{18}$, Gly$^{26}$, Asn$^{36}$, Glu$^{40}$]-oCRF(2-41) having the formula: Gln-Glu-Pro-Pro-Ile-Ser-Leu-Asp-Leu-Thr-Phe-His-Leu-Leu-Arg-Glu-Xaa-Leu-Glu-Met-Thr-Lys-Ala-Asp-Gly-Leu-Ala-Gln-Gln-Ala-His-Ser-Asn-Arg-Asn-Leu-Leu-Asp-Glu-Ala (SEQ ID NO:30), wherein the C-terminus is amidated, and Xaa is Nle, is synthesized. This peptide is likewise considered to stimulate the secretion of ACTH and β-END-LI and to cause a very significant lowering of blood pressure.

EXAMPLE XXXVII

The synthesis of [Arg$^{21}$]-rCRF having the formula: Ser-Glu-Glu-Pro-Pro-Ile-Ser-Leu-Asp-Leu-Thr-Phe-His-Leu-Leu-Arg-Glu-Val-Leu-Glu-Arg-Ala-Arg-Ala-Glu-Gln-Leu-Ala-Gln-Gln-Ala-His-Ser-Asn-Arg-Lys-Leu-Met-Glu-Ile-Ile (SEQ ID NO:31), wherein the C-terminus is amidated, is synthesized. This peptide is likewise considered to stimulate the secretion of ACTH and β-END-LI and to cause a very significant lowering of blood pressure.

EXAMPLE XXXVIII

The synthesis of [Asn³⁶]-rCRF having the formula: Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Asn-Leu-Met-Glu-Ile-Ile (SEQ ID NO:32), wherein the C-terminus is amidated, is synthesized. This peptide is likewise considered to stimulate the secretion of ACTH and β-END-LI and to cause a very significant lowering of blood pressure.

EXAMPLE XXXIX

The peptide [Gly²⁶]-rCRF having the formula: Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gly-Leu-Ala-Gln-Gln-Ala-His-Ser-Asn-Arg-Lys-Leu-Met-Glu-Ile-Ile (SEQ ID NO:33), wherein the C-terminus is amidated, is synthesized. This peptide is likewise considered to stimulate the secretion of ACTH and β-END-LI and to cause a very significant lowering of blood pressure.

EXAMPLE XL

The synthesis of [Leu³²]-rCRF having the formula: Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-Leu-Ser-Asn-Arg-Lys-Leu-Met-Glu-Ile-Ile (SEQ ID NO:34), wherein the C-terminus is amidated, is synthesized. This peptide is likewise considered to stimulate the secretion of ACTH and β-END-LI and to cause a very significant lowering of blood pressure.

EXAMPLE XLI

The peptide [Ile³³]-rCRF having the formula: Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ile-Asn-Arg-Lys-Leu-Met-Glu-Ile-Ile (SEQ ID NO:35), wherein the C-terminus is amidated, is synthesized. This peptide is likewise considered to stimulate the secretion of ACTH and β-END-LI and to cause a very significant lowering of blood pressure.

EXAMPLE XLII

The synthesis of [Met²⁴]-rCRF having the formula: Ser-Glu-Glu-Pro-Pro-Ile-Ser-Leu-Asp-Leu-Thr-Phe-His-Leu-Leu-Arg-Glu-Val-Leu-Glu-Met-Ala-Arg-Met-Glu-Gln-Leu-Ala-Gln-Gln-Ala-His-Ser-Asn-Arg-Lys-Leu-Met-Glu-Ile-Ile (SEQ ID NO:36), wherein the C-terminus is amidated, is synthesized. This peptide is likewise considered to stimulate the secretion of ACTH and β-END-LI and to cause a very significant lowering of blood pressure.

EXAMPLE XLIII

The synthesis of [Met¹⁴]-rCRF having the formula: Ser-Glu-Glu-Pro-Pro-Ile-Ser-Leu-Asp-Leu-Thr-Phe-His-Met-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile (SEQ ID NO:37), wherein the C-terminus is amidated, is synthesized. This peptide is likewise considered to stimulate the secretion of ACTH and β-END-LI and to cause a very significant lowering of blood pressure.

EXAMPLE XLIV

The peptide having the formula: H-D-Tyr-Pro-Pro-Ile-Ser-Leu-Asp-Leu-Thr-Phe-His-Leu-Leu-Arg-Glu-Nle-Leu-His-Nle-Ala-Lys-Ala-Glu-Gly-Glu-Ala-Glu-Gln-Ala-Leu-Leu-Asn-Arg-Asn-Leu-Leu-Glu-Glu-Ala-NH₂ is synthesized. This peptide is likewise considered to stimulate the secretion of ACTH and β-END-LI and to cause a very significant lowering of blood pressure.

EXAMPLE XLV

The peptide having the formula: Pro-Pro-Ile-Ser-Leu-Asp-Leu-Thr-Phe-His-Leu-Leu-Arg-Glu-Xaa-Leu-His-Xaa-Ala-Arg-Ala-Glu-Gln-Glu-Ala-Glu-Gln-Ala-Leu-Leu-Asn-Arg-Asn-Leu-Leu-Glu-Glu-Ala (SEQ ID NO:38), wherein the C-terminus is amidated, and Xaa is Nle, is synthesized. This peptide is likewise considered to stimulate the secretion of ACTH and β-END-LI and to cause a very significant lowering of blood pressure.

EXAMPLE XLVI

The synthetic peptide having the formula: Ser-Gln-Glu-Pro-Pro-Ile-Ser-Leu-Asp-Leu-Thr-Phe-His-Met-Leu-Arg-Glu-Met-Leu-His-Met-Ala-Lys-Met-Glu-Gln-Glu-Ala-Glu-Gln-Ala-Ala-Leu-Asn-Arg-Leu-Leu-Leu-Glu-Glu-Ala (SEQ ID NO:39), wherein the C-terminus is amidated, is synthesized using a procedure generally as set forth in Example I. This peptide is likewise considered to stimulate the secretion of ACTH and β-END-LI and to cause a very significant lowering of blood pressure.

EXAMPLE XLVII

The synthetic peptide having the formula: Ser-Gln-Glu-Pro-Pro-Ile-Ser-Leu-Asp-Leu-Thr-Phe-His-Leu-Leu-Arg-Glu-Met-Leu-His-Arg-Ala-Lys-Ala-Glu-Gln-Glu-Ala-Glu-Gln-Ala-Ala-Ile-Asn-Arg-Leu-Leu-Leu-Glu-Glu-Ala (SEQ ID NO:40), wherein the C-terminus is amidated, is synthesized using a procedure generally as set forth in Example I. This peptide is likewise considered to stimulate the secretion of ACTH and β-END-LI and to cause a very significant lowering of blood pressure.

CRF analogs exhibit such lowering of blood pressure that they may be particularly valuable for the treatment of high blood pressure conditions and also for the treatment of patients who are to undergo certain types of surgery.

CRF profoundly stimulates the pituitary-adrenalcortical axis, and CRF analogs should be useful to stimulate the functions of this axis in some types of patients with low endogenous glucocorticoid production. For example, CRF should be useful in restoring pituitary-adrenal function in patients having received exogenous glucocorticoid therapy whose pituitary-adrenalcortical functions remain suppressed Most other regulatory peptides have been found to have effects upon the central nervous system and upon the gastrointestinal tract. Because ACTH and β-END secretion is the "sine qua non" of mammal's response to stress, it was not surprising that CRF has significant effects on the brain as a mediator of the body's stress response. Accordingly, CRF should also find application in modifying the mood, learning and behavior of normal and mentally disordered individuals. Because CRF analogs elevate the levels of ACTH, β-END, β-lipotropin, other pro-opiomelanocortin gene products and corticosterone, its administration can be used to induce their effects on the brain and its periphery to thereby influence memory, mood, pain appreciation, etc., and more specifically, alertness, depression and/or anxiety. For example, when administered into the ventricles, CRF increases activity and improves learning performance in rats and thus may function as a natural stimulant.

CRF analogs should also be of use for increasing blood flow to the gastrointestinal tract of mammals, particularly humans and other mammals. All CRF related peptides have been shown to dilate the mesenteric vascular bed. Also, oCRF inhibits gastric acid production, and CRF analogs are expected to also be effective in the treatment of gastric ulcers by reducing gastric acid production and/or inhibiting gastrointestinal functions in a mammal.

CRF analogs or the nontoxic addition salts thereof, combined with a pharmaceutically or veterinarily acceptable carrier to form a pharmaceutical composition, may be administered to mammals, including humans, either intravenously, subcutaneously, intramuscularly, percutaneously, e.g. intranasally, intracerebrospinally or orally. The peptides should be at least about 90% pure and preferably should have a purity of at least about 98%; however, lower purities are effective and may well be used with mammals other than humans. This purity means that the intended peptide constitutes the stated weight of all like peptides and peptide fragments present. Administration to humans may be employed by a physician to lower blood pressure or to stimulate endogenors gluco-corticoid production. The required dosage will vary with the particular condition being treated, with the severity of the condition and with the duration of desired treatment.

These peptides may also be used to evaluate hypothalamic pituitary adrenal function in mammals with suspected endocrine or central nervous system pathology by suitable administration followed by monitoring body functions. For example, administration may be used as a diagnostic tool to evaluate Cushing's disease and affective disorders, such as depressive illness.

Such peptides are often administered in the form of pharmaceutically or veterinarily acceptable nontoxic salts, such as acid addition salts or metal complexes, e.g., with zinc, iron, calcium, barium magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 1 to about 200 micrograms of the peptide per kilogram of the body weight of the host animal. In some instances, treatment of subjects with these peptides can be carried out in lieu of the administration of ACTH or corticosteroids, in such instances a dosage as low as about 10 ng/Kg of body weight may be employed. As used herein all temperatures are C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the analogs. It appears important that the amino acid sequence from about positions 6 through 41 or an equivalent sequence of that length be present in the synthetic peptide, whereas the remainder cf the N-terminus of the molecule does not appear as critical. In addition, instead of the simple amide at the C-terminus, a lower alkyl-substituted amide, e.g. methylamide, ethylamide, etc. may be incorporated, and such substituted amides are considered equivalent to the unsubstituted amide. Likewise from one to ten additional amino acid residues can be included at the N-terminus without significantly adversely affecting biological potency. Such peptides are considered as equivalents which fall within the scope of the invention.

Various features of the invention are emphasized in the claims which follow.

What is claimed is:

1. A CRF agonist peptide having either the formula:
Y-Ser-Glu-Glu-Pro-Pro-Ile-Ser-Leu-Asp-Leu-Thr-Phe-His-Leu-Leu-Arg-Glu-Val-Leu-His-$Xaa_{21}$-Ala-Arg-Ala-Glu-$Xaa_{26}$-Leu-Ala-Gln-Gln-Ala-$Xaa_{32}$-Ser-Asn-Arg-$Xaa_{36}$-Leu-$Xaa_{38}$-Glu-Ile-Ile-$NH_2$, or the formula: Y-Ser-Gln-Glu-Pro-Pro-Ile-Ser-Leu-Asp-Leu-Thr-Phe-His-Leu-Leu-Arg-Glu-Val-Leu-His-$Xaa_{21}$-Thr-Lys-Ala-Asp-$Xaa_{26}$-Leu-Ala-Gln-Gln-Ala-$Xaa_{32}$-Ser-Asn-Arg-$Xaa_{36}$-Leu-$Xaa_{38}$-Asp-Ile-Ala-$NH_2$
wherein Y at the N-terminus is hydrogen or an acyl group having 7 or less carbon atoms; from 1 to 5 residues can be deleted in sequence beginning at the N-terminus; $Xaa_{21}$ is Met, Arg or Nle; $Xaa_{26}$ is Gln or Gly; $Xaa_{32}$ is His or Leu; $Xaa_{36}$ is Lys or Asn; and $Xaa_{38}$ is Met, Leu or Nle, or a nontoxic addition salt thereof.

2. A peptide according to claim 1 wherein $Xaa_{36}$ is Asn.

3. A peptide according to claim 1 having the formula: [$His^{20}$, $Asn^{36}$]-oCRF.

4. A peptide according to claim 1 having the formula: [$His^{20}$, $Nle^{21}$]-oCRF.

5. A peptide according to claim 1 having the formula: [$D$-$Pro^4$, $His^{20}$]-oCRF.

6. A peptide according to claim 1 having the formula: [$His^{20}$]-rCRF.

7. A peptide according to claim 1 having the formula: [$His^{20}$, $Gly^{26}$]-rCRF.

8. A peptide according to claim 1 wherein $Xaa_{21}$ is Nle.

9. A peptide according to claim 1 wherein the first 3 residues at the N-terminus are deleted and the N-terminus is acetylated.

10. A peptide according to claim 1 selected from the class consisting of [$His^{20}Nle^{21}$, $Leu^{38}$]-rCRF, [$His^{20}$, $Nle^{21}$, ]-oCRF, [$His^{20}$, $Nle^{21}$]-rCRF, and [$His^{20}$, $Leu^{38}$]-rCRF.

11. A peptide according to claim 1 having the formula: SEQ ID NO:5, wherein Xaa is Nle.

12. A peptide according to claim 11 wherein the 3 residues at the N-terminus are deleted and the N-terminus is acetylated.

13. A CRF agonist peptide selected from the group consisting of SEQ ID NO:2, SEQ ID NO:3 and SEQ ID NO:4.

14. A peptide having the formula: [Ac-$Pro^4$, $His^{20}$, $Nle^{21}$, $Leu^{38}$]-rCRF(4-41) or a nontoxic addition salt thereof.

15. A composition for lowering the blood pressure of mammals comprising an effective amount of a synthetic CRF peptide or a nontoxic addition salt thereof in accordance with claim 1 and a pharmaceutically or veterinarily acceptable liquid or solid carrier therefor.

16. A method of modulating the secretion of ACTH and corticosteroids or the secretion of $\beta$-END-LI, and other pro-opiomelanocortin gene products which comprises administering an effective amount of the CRF agonist peptide of claim 1.

* * * * *

UNITED STATES PATENT AND TRADEMARK OFFICE
CERTIFICATE OF CORRECTION

PATENT NO. : 5,112,809
DATED : May 12, 1992
INVENTOR(S) : Rivier, et al

Page 1 of 2

It is certified that error appears in the above-indentified patent and that said Letters Patent is hereby corrected as shown below:

IN THE ABSTRACT: Line 8, "N-terminals" should be --N-terminal--; Line 16, "mammels" should be --mammals--.

Column 1, line 9, after "1988,", insert --now abandoned,--; Column 3, line 40, "Clu" should be --Glu--; Column 3, line 42, "Cln" should be --Gln--; Column 3, line 45, "Cly" should be --Gly--; Column 3, line 46, "Clu" should be --Glu--; Column 3, line 49, "[Gly$^{20}$]-rCRF," should be --[Gly$^{26}$]-rCRF,--; Column 4, line 41, "R$_1$(X$^5$" should be --R$_{17}$(X$^5$--; Column 5, line 13, "X$^5$" should be --X$^4$--; Column 5, line 53, "chair" should be --chain--; Column 6, line 1, "cf" should be --of--; Column 7, line 15, delete "X$^1$,"; Column 10, line 37, "Arg$^{30}$" should be --Arg$^{36}$--; Col. 13, line 1, after "formula:", insert -- Ser-Gln-Glu-Pro-Pro-Ile-Ser-Leu-Asp-Leu-Thr-Phe-His --;
Col. 17, line 30, after "weight", insert --%--; Column 17, line 33, "endogenors" should be --endogenous--; Column 18, line 39, "cf" should be --of--.

UNITED STATES PATENT AND TRADEMARK OFFICE
CERTIFICATE OF CORRECTION

PATENT NO. : 5,112,809
DATED : May 12, 1992
INVENTOR(S) : Rivier, et al

It is certified that error appears in the above-indentified patent and that said Letters Patent is hereby corrected as shown below:

IN THE CLAIMS: Claim 10, column 54, line 4, " $[His^{20}Nle^{21}, Leu^{38}]$ should be --$[His^{20}, Nle^{21}, Leu^{38}]$ --.

Signed and Sealed this

Twenty-fourth Day of August, 1993

Attest:

BRUCE LEHMAN

Attesting Officer    Commissioner of Patents and Trademarks